(12) United States Patent
Allen et al.

(10) Patent No.: US 6,930,441 B2
(45) Date of Patent: Aug. 16, 2005

(54) SPARK CHECKER-SPARK ARC GAGE

(75) Inventors: Rex H. Allen, Douglass, KS (US); Kevin J. Steen, Augusta, KS (US)

(73) Assignee: The Boeing Company, Chicago, IL (US)

( * ) Notice: Subject to any disclaimer, the term of this patent is extended or adjusted under 35 U.S.C. 154(b) by 275 days.

(21) Appl. No.: 10/274,561

(22) Filed: Oct. 21, 2002

(65) Prior Publication Data

US 2004/0119478 A1 Jun. 24, 2004

(51) Int. Cl.$^7$ ............................................. H01T 13/00
(52) U.S. Cl. ...................... 313/11.5; 313/120; 313/125; 361/253; 361/261
(58) Field of Search ........................ 313/11.5, 118–128, 313/131 A, 141, 142; 361/247, 253, 257, 261

(56) References Cited

U.S. PATENT DOCUMENTS 5,879,215 A * 3/1999 Duffy et al. .................... 445/3
2001/0005117 A1 * 6/2001 Nishida et al. ......... 315/111.11

* cited by examiner

*Primary Examiner*—Tuyet Thi Vo
(74) *Attorney, Agent, or Firm*—Artz & Artz, PC

(57) ABSTRACT

An arc gage (30) includes a non-electrically conductive housing (42) and a first electrically conductive pin (44) that is disposed therein. The first pin (44) has a first end (44A) disposed within the housing (42) and a second end (44B) disposed outside the housing (42). A second electrically conductive pin (46) that has a third end (46A) within the housing (42) and spaced apart from the first end (44A) forms a gap (52) therebetween. A fourth end (46B) of the second electrically conductive pin (46) is disposed outside the housing (42). The arc gage (30) may be a stand alone device or used as part of a spark checking device that includes a device housing a voltage generator and a wand (26) that is electrically coupled to the power terminal of a voltage generator (34) disposed within the device housing (28).

23 Claims, 2 Drawing Sheets

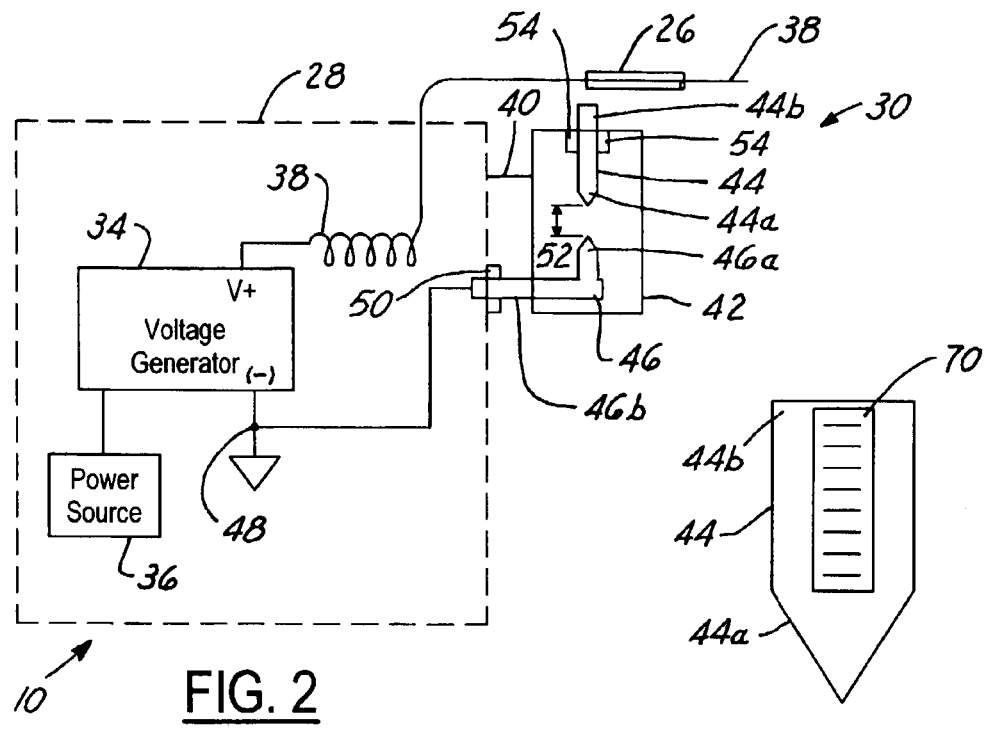
FIG. 2
FIG. 4
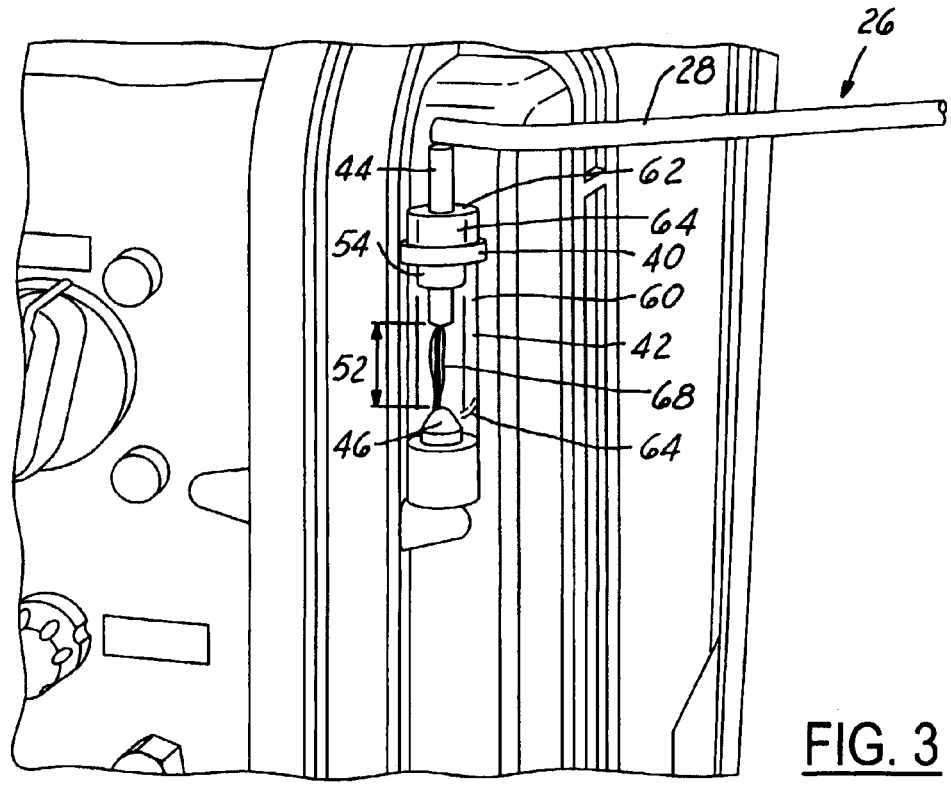
FIG. 3

SPARK CHECKER-SPARK ARC GAGE

TECHNICAL FIELD

The present invention relates generally to chemical milling processes, and more specifically, to a method for checking the consistency of masking used in the chemical milling process.

BACKGROUND ART

Aircraft typically use aluminum skin panels to make up the exterior of the fuselage. Each skin panel typically has thick portions and thin portions. To form the thin portions, a gage reduction operation is performed. The gage reduction typically used is chemical milling. Chemical milling uses a caustic solution in a dip tank to remove a specific pattern and thickness of aluminum from the interior surface of the skin. Then, a phosphoric anodized acid operation is conducted at another dip tank to prepare the interior surface for painting. A protective spray maskant is applied to both the interior and exterior of the panel to provide these operations. The areas of the skin panel that require chemical milling and phosphoric anodized acid exposure are not applied with maskant or have the maskant removed in the specific engineering pattern required. The protective spray maskant is not a perfectly sealed surface and suffers from voids, air bubbles, and is occasionally damaged during the handling of the large skin panels. If not repaired, the imperfections in the protective skin maskant will allow the caustics and acids in the dip tanks to attack the skin panel. Such panels must be scrapped. Each panel is on the order of thousands of dollars.

To uncover any imperfections in the protective maskant, a spark checking operation is typically performed. A spark checker uses a high-voltage electrical current to uncover voids, damage and thin spots in the protective maskant. The operator of a spark check guides a wand across the maskant surface. Any imperfections allow an electrical current to arc through to the aluminum skin panel. These areas are then easily identified and may then be repaired.

Spark checker devices must produce a proper voltage to generate the arc. Most spark checkers are battery operated and rely on a coil to achieve the proper voltage at the wand. As the battery runs down, it is difficult for the operator to be sure if enough voltage is being generated to allow the unit to function properly. One type of device is known as a "holiday detector." Such devices have a digital voltmeter that is used to read the voltage being generated. However, the digital voltmeter has readings that jump erratically and thus, it is difficult to use. The voltmeter is typically connected to the battery and not to the wand itself. Therefore, the operator does not know if the coil is functioning properly or if the cord connections to the wand are secure. Other spark check devices do not provide any indication of voltage on the system. Such systems have been blamed for missing maskant imperfections. One problem with providing a high-voltage voltmeter is that typically the readings are erratic and difficult to monitor. Voltmeters are also relatively expensive.

It would therefore be desirable to provide a reliable and inexpensive way in which to determine if a sufficient voltage to check for maskant defects is being generated by a spark checker.

SUMMARY OF THE INVENTION

The present invention provides a device that may be easily used to determine if a sufficient amount of voltage is present in a wand of a protective coating checking device.

In one aspect of the invention, an arc gage includes a non-electrically conductive housing and a first electrically conductive pin that is disposed within the housing. The pin has a first end disposed within the housing and a second end disposed outside the housing. A second electrically conductive pin that has a third end within the housing and spaced apart from the first end forms a gap therebetween. A fourth end of the second electrically conductive pin is disposed outside the housing. The arc gage may be a standalone device or used as part of a spark checking device that includes a device housing a voltage generator and a wand that is electrically coupled to the power terminal of a voltage generator disposed within the device housing.

In a further aspect of the invention, a method of testing the voltage in spark checking device comprises providing a voltage at a wand, providing an arc checker having a first pin, a second pin and a gap between the first pin and the second pin, applying the wand to a first pin, when the voltage is high, generating a spark across the gap; and when the voltage is low, not generating a spark across the gap.

One advantage of the invention is that the arc gage may be incorporated easily onto existing devices as well as incorporated into newly manufactured devices. Another advantage of the invention is that the device is relatively inexpensive and provides a clear indication as to the voltage checker at the wand itself rather than the battery within the device.

Other aspects and advantages of the present invention will become apparent upon the following detailed description and appended claims, and upon reference to the accompanying drawings.

BRIEF DESCRIPTION OF THE DRAWINGS

FIG. 2 is a high level electrical schematic view of the device according to the present invention.

FIG. 3 is a perspective view of an arc checker formed according to the present invention.

FIG. 4 is an alternative device for the first electrode of FIGS. 1, 2, and 3.

BEST MODES FOR CARRYING OUT THE INVENTION

Figure 1:
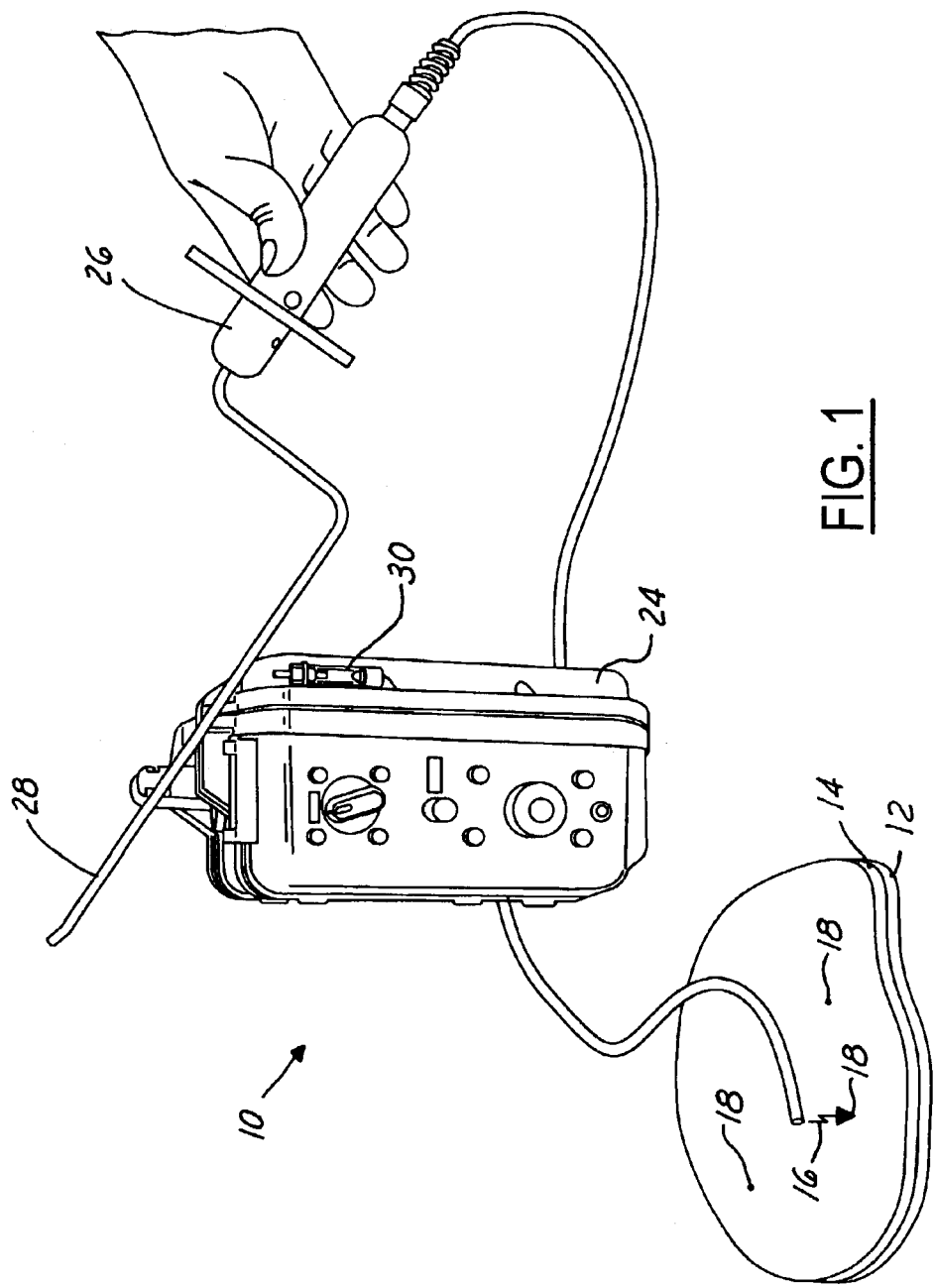
FIG. 1 is a perspective view of a spark checking device formed according to the present invention.

In the following figures the same reference numerals will be used to identify the same components.

In the following figures the arc checking device is used to detect irregularities in a masking on an airplane skin. However, the present invention is applicable to various types of coatings and various types of applications. For example, the device may be used to check for the presence or absence of paint, films and other protective coatings.

Referring now to FIG. 1, a spark checking device 10 is illustrated with respect to a portion of an airplane fuselage skin 12 having a coating 14 thereon. Spark checking device 10 as illustrated is shown generating an arc 16 in response to a void 18 or other irregularity in coating 14. Coating 14 may, for example, be a masking used in the chemical milling process. By finding the voids 18, the coating 14 may be easily repaired to prevent damage to skin 12 during the manufacturing process. Spark checking device 10 has a housing 24. Housing 24 is electrically coupled to a wand 26 that has an electrode 28 coupled thereto. Electrode 28 is electrically coupled to the voltage generator (not shown) and is used to generate a voltage therefrom.

Housing 24 has an arc gage 30 coupled thereto. Arc gage 30 is used to test the sufficiency of the voltage at electrode 28 so that voids 18 or other irregularities may be found. When a sufficient voltage is present at gage 30, a spark is generated. The spark provides an easily visible indication of proper operating conditions of wand 26.

Referring now to FIG. 2, a simplified electrical schematic of the spark checking device 10 is illustrated. Spark checking device 10 has a voltage generator 34 that is coupled to a power source 36. Power source 36 may be AC by way of a common cord and plug or DC by way of a battery located within housing 28. Voltage generator 34 is coupled to a coil 38 that allows a sufficient voltage and a sufficient current to determine whether voids or other irregularities exist within a coating.

Arc gage 30 is coupled by means of a fastener 40 to housing 42. In this illustration, fastener 40 is a wire tie. Housing 42 may be fixably mounted to housing 24 using various types of fasteners including epoxy, screw, or other types of strapping. Arc gage 30 has a housing 42 that is used to house a first pin 44 and a second pin 46. First pin 44 has a first end 44A and a second end 44B. First end 44A may be conical in shape and extends within housing 42. Second end 44B extends outside of housing. In one constructed embodiment, pin 44 was constructed of 3/16 inch diameter stainless steel and has an approximately one inch end 44B extending from housing 42. Pin 46 has a first end 46A that may also be shaped in a conical shape in a similar manner to that of end 44A. Pin 46 also has a second end 46B that extends from housing 42. Housing 42 is preferably coupled to a ground terminal 48 of voltage generator 34. End 46B may also be threaded so that a nut 50 may be used to fasten it to housing 24. End 46B is shown having a right angle bend therein so that it extends through the side of housing 289. Of course, pin 46 may be straight like pin 44. Ends 44A and 46A are spaced apart so that a gap 52 is disposed therebetween. Gap 52 may have varying sizes depending on the amount of voltage to be detected from electrode 28. In one constructed embodiment, the position and spacing of gap 52 was fixed. However, a variable gap may also be provided by allowing for the adjustment of at least one of the pins 44, 46 as will be further described below in FIG. 4.

A nylon shim 54 may also be used to help locate electrode 44 within housing 42. Shim 54 can also be configured to allow for the adjustment of pin in and out axially or radially within housing.

In a constructed embodiment, housing 42 was constructed of acrylic. However, those skilled in the art will recognize that other types of transparent and semi-transparent, non-conductive housings may be used. When electrode 28 touches electrode 44, and a spark is not generated through gap 52, the device may be sent to be repaired or recharged and is not used to check voids.

Referring now to FIG. 3, housing 42 is illustrated as cylindrical having an axial wall 60 extending therearound and a pair of radial walls 62. It should also be noted that a vent 64 may be disposed in either or both of the radial wall 62 or axial wall 60. This may prevent the buildup of heat or pressure therein.

Referring now to FIG. 4, first pin 44 is illustrated having a depth gauge 70 thereon. Depth gauge 70 is calibrated to provide various gaps. Thus, a common electrode may be manufactured for different types of devices having various voltages. The depth may be adjusted and fixed into place by shim. Other ways in which to hold electrode in place may be adhesive or threads.

As illustrated in FIG. 3, a sufficient voltage potential difference is provided between electrode 28 and pin 44 and pin 46 so that an arc 68 is generated therebetween.

In operation, a voltage is generated by voltage generator 34, which in turn creates a voltage at electrode 28 of wand 26. To check for a sufficient voltage to detect voids or other irregularities in a protective coating, the electrode 28 contacts pin 44. When a voltage level is high, enough to detect a void, an arc 68 is generated across gap 52 between pins 44 and 46. When the voltage is low, no spark is generated across gap 52. The arc gage 30 is preferably fixably coupled to housing 24 so that the pin 46 maintains the ground potential. Thus, at several times during testing, the voltage at the wand 26 may be easily checked.

While the invention has been described in connection with one or more embodiments, it should be understood that the invention is not limited to those embodiments. The invention is intended to cover all alternatives, modifications, and equivalents, as may be included within the spirit and scope of the appended claims.

What is claimed is:

1. An arc gauge comprising:
   a non-electrically conductive housing comprising a vent hole therethrough;
   a first electrically conductive pin having a first end disposed within the housing and a second end disposed outside the housing; and
   a second electrically conductive pin having a third end disposed within the housing and spaced apart from said first end to form a gap therebetween and a fourth end disposed outside the housing.

2. An arc gauge as recited in claim 1 wherein said housing is formed of acrylic.

3. An arc gauge as recited in claim 1 wherein said housing is transparent.

4. An arc gauge as recited in claim 1 wherein said first pin and said second pin are composed of stainless steel.

5. An arc gauge as recited in claim 1 further comprising a shim positioning said first pin within said tube.

6. An arc gauge as recited in claim 1 further comprising a shim positioning said first pin within said tube.

7. An arc gauge as recited in claim 1 wherein said housing is cylindrical having an axial wall and at least one radial wail.

8. An arc gauge as recited in claim 3 wherein the first end of the first pin comprises a first conical end thereon.

9. An arc gauge as recited in claim 8 wherein the third end of the second pin comprises a second conical end thereon.

10. An arc gauge as recited in claim 1 wherein said housing is cylindrical having an axial wall and at least one radial wall.

11. An arc gauge as recited in claim 10 wherein said vent hole is disposed on the axial wail.

12. An arc gauge as recited in claim 10 wherein said vent hole is disposed on the at least one radial wall.

13. A spark checking device comprising:
   a device housing;
   a voltage generator disposed within the housing, said voltage generator having a power terminal and a ground terminal;
   a wand electrically coupled to the power terminal;
   an arc gauge coupled to the device housing, said arc gauge comprising,
      a non-electrically conductive housing having a vent hole therethrough;
      a first pin having a first end disposed within the housing and a second end disposed outside the housing; and a second pin having a third end disposed within the housing and spaced apart from said first end to form a gap therebetween and a fourth end disposed outside the housing, said third pin electrically coupled to said negative terminal so that when the wand has a predetermined voltage, an arc is generated across the gap.

14. A spark checking device as recited in claim 13 wherein the first end of the first pin comprises a first conical end and the third end of the second pin comprises a second conical end.

15. An arc gauge as recited in claim 13 wherein said housing is cylindrical having an axial wall and at least one radial wall.

16. A spark checking device as recited in claim 15 wherein said vent hole is disposed through the axial wall.

17. A spark checking device as recited in claim 15 wherein said vent hole is disposed through the at least one radial wall.

18. A method of testing the voltage in a spark checking device comprising:

providing a voltage at a wand;

providing an arc checker having a first pin, a second pin and a gap between the first pin and the second pin;

applying the wand to a first pin;

when the voltage is high, generating a spark across the gap; end when the voltage is low, not generating a spark across the gap.

19. A method as recited in claim 18 wherein the high voltage corresponds to a voltage sufficient enough to detect irregularities in a protective coating.

20. A method as recited in claim 18 further comprising coupling a second pin to a ground potential.

21. A method as recited in claim 18 wherein providing an arc checker comprises providing said arc checker having a housing comprising a vent hole therethrough.

22. A method as recited in claim 21 wherein said vent hole is disposed on the axial wall.

23. A method as recited in claim 21 wherein said vent hole is disposed on the at least one radial wall.

* * * * *